United States Patent [19]

Samanen

[11] Patent Number: 5,602,145
[45] Date of Patent: Feb. 11, 1997

[54] BICYCLIC FIBRINOGEN ANTAGONISTS

[75] Inventor: James Samanen, Phoenixville, Pa.

[73] Assignee: Smithkline Beecham Corporation, Philadelphia, Pa.

[21] Appl. No.: 445,986

[22] Filed: May 22, 1995

Related U.S. Application Data

[63] Continuation of Ser. No. 222,202, Apr. 1, 1994, abandoned, which is a continuation of Ser. No. 74,248, Jun. 9, 1993, abandoned.

[51] Int. Cl.$^6$ .................. C07D 217/24; A61K 31/47
[52] U.S. Cl. ............................................ 514/309; 546/141
[58] Field of Search ..................... 514/309; 546/141

[56] References Cited

U.S. PATENT DOCUMENTS

| | | | |
|---|---|---|---|
| 5,116,985 | 5/1992 | Takeshita | 546/141 |
| 5,260,316 | 11/1993 | Van Duzer et al. | 514/309 |
| 5,338,851 | 8/1994 | Huff et al. | 546/141 |

OTHER PUBLICATIONS

Banner, Perspect. Med. Chem., pp. 27–43, 1993.
Shuman, J. Med. Chem., vol. 36, pp. 314–319, 1993.
Thrombosis and Haemostasis, vol. 70(1), pp. 94–98 (1993), Topol et al.
Coronary Artery Disease, vol. 3, No. 11, pp. 1016–1029 (1992), Coller.
J. of Pharmacology and Experimental Therapeutics, vol. 270, No. 2, pp. 614–621 (1994), Nichols.
TIPS, vol. 13, pp. 413–417 (1992), Nichols et al.
Chemical Abstracts, vol. 93, No. 5, p. 910 (1980).
Chemical Abstracts, vol. 76, No. 1, pp. 3667–3668 (1972).

*Primary Examiner*—C. Warren Ivy
*Assistant Examiner*—D. Margaret M. Mach
*Attorney, Agent, or Firm*—Mary McCarthy; Stephen Venetianer; Edward T. Lentz

[57] ABSTRACT

This invention relates to compounds of the formula:

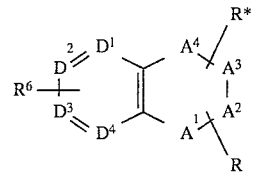

which are effective for inhibiting platelet aggregation, pharmaceutical compositions for effecting such activity, and a method for inhibiting platelet aggregation.

9 Claims, No Drawings

BICYCLIC FIBRINOGEN ANTAGONISTS

This is a continuation of application Ser. No. 08/222,202, filed Apr. 1, 1994, now abandoned which is continuation of application Ser. No. 08/074,248, filed Jun. 9, 1993, now abandoned.

FIELD OF THE INVENTION

This invention relates to novel bicyclic compounds which inhibit platelet aggregation, pharmaceutical compositions containing the compounds and methods of using the compounds.

BACKGROUND OF THE INVENTION

Platelet aggregation is believed to be mediated primarily through the fibrinogen receptor, or GPIIb-IIIa platelet receptor complex, which is a member of a family of adhesion receptors referred to as integrins. It has been found that frequently the natural ligands of integrin receptors are proteins which contain an Arg-Gly-Asp sequence. Von Willebrand factor and fibrinogen, which are considered to be natural ligands for the GPIIb-IIIa receptor, possess an Arg-Gly-Asp (RGD in single letter amino acid code) sequence in their primary structure. Functionally, these proteins are able to bind and crosslink GPIIb-IIIa receptors on adjacent platelets and thereby effect aggregation of platelets.

Fibronectin, vitronectin and thrombospondin are RGD-containing proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Linear and cyclic peptides which bind to vitronectin and contain an RGD sequence are disclosed in WO 89/05150 (PCT US88/04403). EP 0 275 748 discloses linear tetra- to hexapeptides and cyclic hexa- to octapeptides which bind to the GPIIb-IIIa receptor and inhibit platelet aggregation. Other linear and cyclic peptides, the disclosure of which are incorporated herein by reference, are reported in EP-A 0 341 915. However, the peptide like structures of such inhibitors often pose problems, such as in drug delivery, metabolic stability and selectivity. Inhibitors of the fibrinogen receptor which are not constructed of natural amino acid sequences are disclosed in EP-A 0 372,486, EP-A 0 381 033 and EP-A 0 478 363. WO 92/07568 (PCT/US91/08166) discloses fibrinogen receptor antagonists which mimic a conformational γ-turn in the RGD sequence by forming a monocyclic seven-membered ring structure. There remains a need, however, for novel fibrinogen receptor antagonists (e.g., inhibitors of the GPIIb-IIIa protein) which have potent in vivo and in vitro effects and lack the peptide backbone structure of amino acid sequences.

The present invention discloses novel bicyclic compounds, including 1,2,3,4-tetrahydroisoquinolines. These compounds inhibit the GPIIb-IIIa receptor and inhibit platelet aggregation.

SUMMARY OF THE INVENTION

In one aspect this invention is a bicyclic compound comprising a substituted six-membered ring fused to an aromatic six-membered ring as described hereinafter in formula (I).

This invention is also a pharmaceutical composition for inhibiting platelet aggregation or clot formation, which comprises a compound of formula (I) and a pharmaceutically acceptable carrier.

This invention is further a method for inhibiting platelet aggregation in a mammal in need thereof, which comprises internally administering an effective amount of a compound of formula (I).

In another aspect, this invention provides a method for inhibiting reocclusion of an artery or vein in a mammal following fibrinolytic therapy, which comprises internally administering an effective amount of a fibrinolytic agent and a compound of formula (I). This invention is also a method for treating stroke, transient ischemia attacks, or myocardial infarction.

DETAILED DESCRIPTION OF THE INVENTION

This invention discloses bicyclic compounds which inhibit platelet aggregation. The novel bicyclic compounds comprise a six-membered ring fused to an aromatic six-membered ring and having a nitrogen-containing substituent on the aromatic six-membered ring and an aliphatic substituent, preferably containing or being an acidic moiety, on the six-membered ring. The six-membered ring may contain heteroatoms, such as nitrogen, oxygen and sulfur, and the aromatic six-membered ring may be carbocyclic or contain up to two nitrogen atoms. The fused 6—6 ring system is believed to interact favorably with the GPIIb-IIIa receptor and to orient the substituent sidechains on the aromatic six and sthe six-membered rings so that they may also interact favorably with the receptor.

Although not intending to be bound to any specific mechanism of action, these compounds are believed to inhibit the binding of fibrinogen to the platelet-bound fibrinogen receptor GPIIb-IIIa, and may interact with other adhesion proteins via antagonism of a putative RGD binding site.

The compounds of this invention are compounds of formula (I):

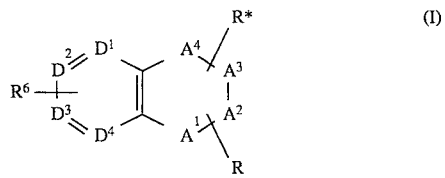

wherein $A^1$ to $A^4$ form an accessible substituted six-membered ring, which may be saturated or unsaturated, optionally containing up to two heteroatoms chosen from the group of O, S and N wherein S and N may be optionally oxidized;

$D^1$ to $D^4$ form an accessible substituted aromatic six-membered ring, optionally containing up to two nitrogen atoms;

R is at least one substituent chosen from the group of $R^7$, or Q-$C_{1-4}$alkyl, Q-$C_{2-4}$alkenyl, Q-$C_{2-4}$alkynyl, optionally substituted by one or more of =O, $R^{11}$ or $R^7$;

R* is H, Q-$C_{1-6}$alkyl, Q-$C_{1-6}$oxoalkyl, Q-$C_{2-6}$alkenyl, Q-$C_{3-4}$oxoalkenyl, Q-$C_{3-4}$oxoalkynyl, Q-$C_{2-4}$alkynyl, $C_{3-6}$cydoalkyl, Ar or Het, optionally substituted by one or more of $R^{11}$;

Q is H, $C_{3-6}$cycloalkyl, Het or Ar;

$R^6$ is $W-(CR'_2)_q-Z-(CR'R^{10})_r-U-(CR'_2)_s-V-$;

$R^7$ is $-COR^8$, $-COCR'_2R^9$, $-C(S)R^8$, $-S(O)_mOR'$, $-S(O)_mNR'R''$, $-PO(OR-)$, $-PO(OR')_2$, $-B(OR')_2$, $-NO_2$ and Tet;

$R^8$ is $-OR'$, $-NR'R''$, $-NR'SO_2R'$, $-NR'OR'$, $-OCR'_2C(O)OR'$, $-OCR'_2OC(O)-R'$, $-OCR'_2C(O)NR'_2$, $CF_3$ or AA;

$R^9$ is $-OR'$, $-CN$, $-S(O)_rR'$, $S(O)_mNR'_2$, $-C(O)R'C(O)NR'_2$ or $-CO_2R'$;

$R^{10}$ is H, $C_{1-4}$alkyl or $-NR'R''$;

$R^{11}$ is H, halo, $-OR^{12}$, $-CN$, $-NR'R^{12}$, $-NO_2$, $-CF_3$, $CF_3S(O)_r-$, $-CO_2R'$, $-CONR'_2$, $Q-C_{0-6}$alkyl-, $Q-C_{1-6}$oxoalkyl-, $Q-C_{2-6}$alkenyl-, $Q-C_{2-6}$alkynyl-, $Q-C_{0-6}$alkyloxy-, $Q-C_{0-6}$alkylamino-or $Q-C_{0-6}$alkyl-$S(O)_r-$;

$R^{12}$ is R', $-C(O)R'$, $-C(O)NR'_2$, $-C(O)OR^{15}$, $-S(O)_mR'$ or $S(O)_mNR'_2$;

$R^{13}$ is R', $-CF_3$, $-SR'$, or $-OR'$;

$R^{14}$ is R', $C(O)R'$, CN, $NO_2$, $SO_2R'$ or $C(O)OR_{15}$;

$R^{15}$ is H, $C_{1-6}$alkyl or Ar-$C_{0-4}$alkyl;

R' is H, $C_{1-6}$alkyl, $C_{3-7}$cycloalkyl-$C_{0-4}$alkyl or Ar-$C_{0-4}$alkyl;

R" is R', $-C(O)R'$ or $-C(O)OR_{15}$; R''' is R" or AA2;

AA1 is an amino add attached through its amino group and having its carboxyl group optionally protected, and AA2 is an amino acid attached through its carboxyl group, and having its amino group optionally protected;

U and V are absent or CO, $CR'_2$, $C(=CR'2)$, $S(O)_n$, O, NR', CR'OR', $CR'(OR'')CR'_2,CR'_2CR'(OR'')$, $C(O)CR'_2,CR'_2C(O)$, $CONR'$, $NR'CO$, $OC(O)$, $C(O)O$, $C(S)O$, $OC(S)$, $C(S)NR'$, $NR'C(S)$, $S(O)_nNR'$, $NR'S(O)_n$, $N=N$, $NR'NR'$, $NR'CR'_2,CR'_2NR'$, $CR'_2O$, $OCR'_2$, $C\equiv C$ or $CR'=CR'$, provided that U and V are not simultaneously absent;

W is $R'R'''N-$, $R'R''NR'N-$, $R'R''NR'NCO-$, $R'_2NR'NC(=NR')-$,

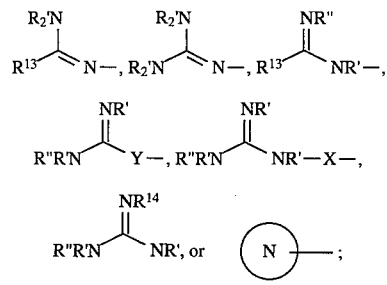

X is $N=CR'$, C(O) or O;

Y is absent, S or O;

Z is $(CH_2)t$, Het, Ar or $C_{3-7}$cycloalkyl;

m is 1 or 2;

n is 0 to 3;

p is 0 or 1;

q is 0 to 3;

r is 0 to 2;

s is 0 to 2; and t is 0 to 2; or pharmaceutically acceptable salts thereof.

Also included in this invention are pharmaceutically acceptable addition salts, complexes or prodrugs of the compounds of this invention. Prodrugs are considered to be any covalently bonded carriers which release the active parent drug according to formula (I) in vivo.

In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may

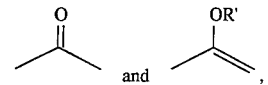

and tautomers of guanidine-type groups, such as

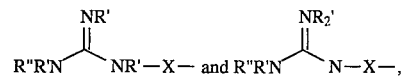

each tautomeric form is contemplated as being included within this invention whether existing in equilibrium or locked in one form by appropriate substitution with R'. The meaning of any substituent at any one occurrence is independent of its meaning, or any other substituent's meaning, at any other occurrence, unless specified otherwise.

With reference to formula (I), suitably, $A^1$ is $CR^1R^1$, $CR^1$, $NR^1$, N, O or $S(O)_x$;

$A^2$ is $CR^2R^2$, $CR^2$ or $NR^2$;

$A^3$ is $CR^3R^3$, $CR^3$ or $NR^3$;

$A^4$ is $CR^4R^4$, $CR^4$, $NR^4$, N, O or $S(O)_x$;

$D^1-D^4$ are $CR^{11}$, $CR^6$ or N;

R is $(CR^{14}R^{15})_u-(T)_v-(CR^{16}R^{17})_w-R^7$ or $=CR'-(T)_v-(CR^{16}R^{17})_w-R^7$ wherein T is $CR^{16}R^{17}-CR^{16}R^{17}$, $CR'=CR'$ or $C\equiv C$, and $R^{16}$ and $R^{17}$ are R', OR'or together are $=O$, provided that $R^{16}$ and $R^{17}$ are not simultaneously OR' when they are attached to the same carbon;

$R^1$ and $R^{1'}$are R* or R, or together are $=O$;

$R^2$ and $R^{2'}$are R*, R or $=O$;

$R^3$ and $R^{3'}$are R*, R or $=O$;

$R^4$ and $R^{4'}$are R*, R or $=O$;

$R^6$ is $W-(CR'_2)_q-Z-(CR'R^{10})_r-U-(CR'_2)_s$;

x is 0 to 2; and u, v and w are 0 or 1.

More suitably, $A^1$ is $CR^1R^1$, $CR^1$, $NR^1$, N, O or S; $A^2$ is $CR^2R^2$, $NR^2$ or $CR^2$; $A^3$ is $CR^3R^3 NR^3$ or $CR^3$; $A^4$ is $CR^4R^4$, $CR^4$, $NR^4$, or N; $D^1$ and $D^4$ are CH; $D^2$ or $D^3$ is $CR^6$; $R^2$ is R; $R^1$, $R^{1'}$, and $R^3$, $R^{3'}$are $=O$ or R*, H; $R^4$, $R^{4'}$are R*, H; $R^6$ is $W-(CR'_2)_q-Z-(CR'R^{10})_r-U$; and v is 0.

Preferably, $A^1$ is $CR^1R^1$ or $CR^1$; $A^2$ is $CR^2$, $CR^2R^{2'}$or $NR^2$; $A^3$ is $CR^3R^{3'}$; $A^4$ is $CR^4R^{4'}$or $NR^4$; $D^1$ and $D^4$ are CH; and $D^2$ or $D^3$ is $CR^6$.

Preferably one of $D^2$ and $D^3$ is $CR^6$ and the other is CH.

Suitably, $(CR'R^{10})_r-U-(CR'_2)_s-V$ is CO, CONR', NR'CO, $CH_2CHOH$, $CHOHCH_2$, $CH_2CH_2$, $CH_2O$, $OCH_2$, $CH=CH$, $C\equiv C$, $CH_2CH=CH$, $(CH_2)_2$, $CH_2CONR'$, $CONR'CH_2$, $CH(NR'R'')CONR'$, $CH_2CH_2NR'CO$, $CONR'CHR'CH_2$, $CH_2NR'CO_2CH_2$, $CONR'CH_2CO$, $CONR'CH_2CHOH$, $CH=CHCONR'$, $(CH_2)_3O$, $NR'CO_2CH=CH$, or $SO_2NR'CHR'CH_2$.

In one embodiment, $A^1$ is $C=O$, $A^2$ is $NR^2$, $A^3$ is $CR^3R^{3'}$and $A^4$ is $CR^4R^{4'}$.

In a more specific embodiment, $A^1$ is $C=O$; $A^2$ is $NR^2$; $A^3$ is $CR^3R^{3'}$; $A^4$ is $CR^4R^{4'}$; $R^2$ is $CH_2CO_2H$ or $CH_2CH_2CO_2H$; $R^3$, $R^{3'}$ is H,H; $R^4$, $R^{4'}$ is H,H; Z is phenyl, a six-membered Het or $(CH_2)t$; W is $R'_2N$, $H_2NC(=NH)$, $H_2NC(=NH)NH$ or ; (N); and $(CR'R^{10})_r$—U—$(CR'_2)_s$—V is $(CR'R^{10})_r$—U— or —U—$(CR'_2)_s$, (e.g., V is absent and s is 0 and one of s and r are 0) wherein U is $CH(NR'R'')CONH$, NR'CO, CONR', CR'=CR', C≡C, O, CO or $CH_2$.

Representative compounds of this invention are given by each of formulas (II)–(III):

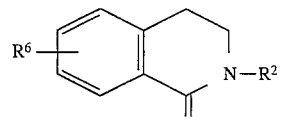
(II)

or

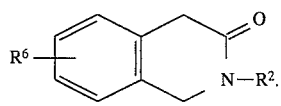
(III)

Generally, $R^2$ is $(CH_2)_{1-3}$—$R^7$. $R^1$ and $R^4$ are chosen from H, $C_{1-6}$alkyl, $C_{1-4}$oxoalkyl, Ar—$C_{0-4}$alkyl and =O, optionally substituted on the alkyl group by one or two $R^{11}$. Generally, $R^{1'}$–$R^{4'}$ are H, or together with their geminal substituent are =O.

Preferably, $R^1$ and $R^{1'}$ are =O.

Preferably, $R^2$ is $R^7$, $CH_2$—$R^7$ or $CH_2CH_2$—$R^7$. More preferably, $R^2$ is $CH_2$—$R^7$ or $CH_2CH_2$—$R^7$ Most preferably, $R^7$ is $CO_2H$.

Preferably, $R^3$ and $R^{3'}$ are H or $C_{1-6}$alkyl.

Preferably, $R^4$ is H, $C_{1-6}$alkyl, Ar-$C_{1-4}$alkyl, $C_{3-6}$cycloalkyl-$C_{1-4}$alkyl, $CH_2CO_2H$ or $CH_2CH_2CO_2H$, and $R^{4'}$ is H.

Suitably $(CR'R^{10})_r$—U—$(CR'_2)_s$—V is $(CR'R^{10})_r$—U— or —U—$(CR'_2)_s$.

Preferably, $(CR'R^{10})_r$—U—$(CR'_2)_s$—V is $(CH_2)_{0-2}NR'CO$, $(CH_2)_{0-2}CONR'$, $(CH_2)_{0-2}CO$, $(CH_2)_{0-2}CH=CH$, $(CH_2)_{0-2}C≡C$, $(CH_2)_{1-3}O$, or $(CH_2)_{1-5}$. More preferably, $(CR'R^{10})_r$—U—$(CR'_2)_s$—V is $(CH_2)0-2NR'CO$ or $(CH_2)0-2CONR'$, where R' is H or methyl. Preferably R' is methyl.

Preferably, Z is phenyl, piperidinyl, piperazinyl or $(CH_2)t$. Suitably t is 1.

Preferably, W is R"R'N—, R"R'NC(=NH) or R"R'NC(=NR')NR'— or (N), wherein R' and/or R" are preferably H.

Particular examples of $R^6$ are:

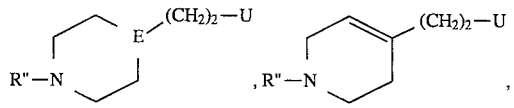

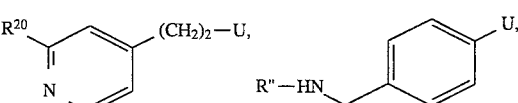

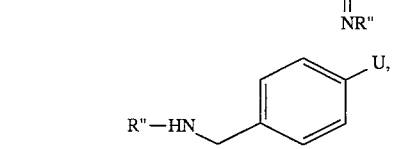

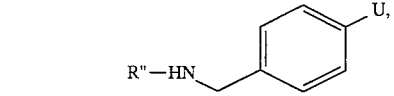

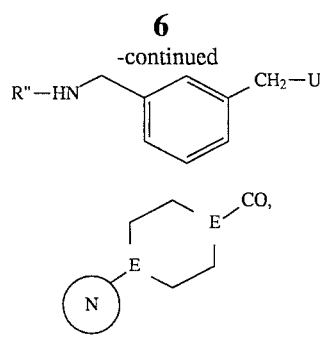

$R"HNC(=NH)NH$—$(CH_2)_3(CHR^{10})$—U, and R"HN—$(CH_2)_5$—U wherein E is N or CH, $R^{20}$ is hydrogen, amino, mono or di-$C_{1-4}$alkylamino, hydroxy or $C_{1-4}$alkyl, and U is NR'CO, CONR', $(CH_2)CO$, CH=CH, $CH_2O$, $OCH_2$ and $(CH_2)_2$.

Preferred illustrative examples of $R^6$ are:

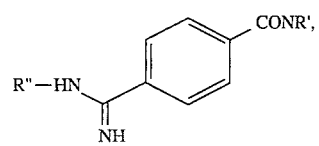

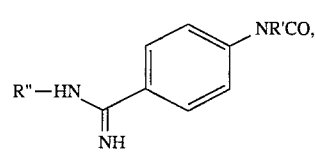

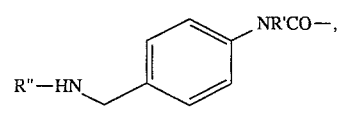

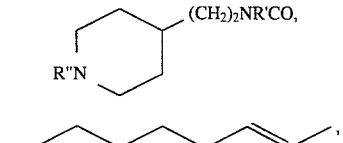

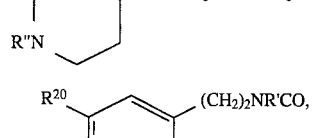

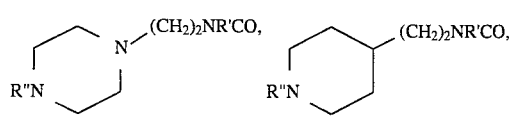

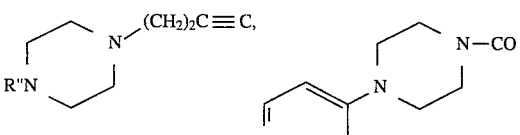

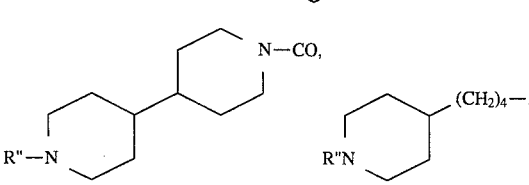

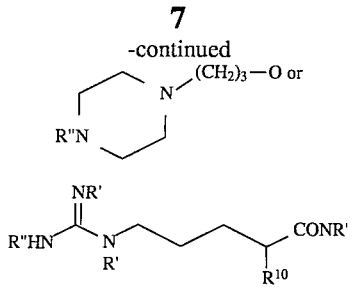

wherein R' are H or C$_{1-4}$alkyl. Preferably R' is methyl and R" is H.

Preferred compounds of this inventions are:

7-[4-(amidinobenzamide]-2-carboxymethyl-1,2,3,4-tetrahydroisoquin

7-[4-(amidinobenzamido]-2-carboxymethyl-1,2,3,4-tetrahydroisoquinolin-1-one, and 7-[4-(amidinobenzamide]-2-carboxymethyl-1,2,3,4-tetrahydroisoquinolin-3-one; or a pharmaceutically acceptable salt thereof.

The most preferred compound of this invention is 7-[4-(amidinobenzamide]-2-carboxymethyl-1,2,3,4-tetrahydroisoquinolin-1-one or a pharmaceutically acceptable salt thereof.

In the above description of formula (I), preferably only one or two of A$^1$ to A$^4$ are substituted by R, and only one of D$^1$–D$^4$ is substituted by R$^6$. W represents a nitrogen-containing group which is capable of making a hydrogen bond. Preferably W is a basic nitrogen moiety. R$^7$ represents a group with a non-bonding pair of electrons which is capable of forming a hydrogen bond or chelating with a metal cation. Preferably R$^7$ is acidic. It is also preferred that 10–15 (most preferably about 13) intervening covalent bonds via the shortest intramolecular path will exist between the group R$^7$ and a terminal basic nitrogen moiety of W for optimal spacing between these groups, and the moieties T, U, V and Z, and the alkyl spacers represented by q, r, s, u, v and w are chosen accordingly. For instance, by way of illustration, but not limitation, when one of R$^2$ or R$^3$ is (CH$_2$)$_2$CO$_2$H, or preferably CH$_2$CO$_2$H, and R$^6$ is a substituent in the 6- or 7-position of the 1,2,3,4-tetrahydroisquinolinone and is W—(CR'$_2$)$_q$—Z—(CR'R$^{10}$)$_r$—U—(e.g., s is 0 and is absent), then: when W is ⓝ preferably a 4-substituted six-membered nitrogen heterocycle), and Z is (CH$_2$)$_t$, and U is chosen from NR'CO, CONR', CH$_2$O, OCH$_2$, CH$_2$CH$_2$, CR'=CR' or C≡C, ('group1'), suitably q+t+r is 1–3 and preferably q+t+r is 1; when W is ⓝ and Z is a six-membered Ar or Het ring (preferably 1,4-disubstituted), and U is O, CH$_2$ or CO, q and r are preferably 0; when W is H$_2$N—and Z is (CH$_2$)$_t$, and U is chosen from group 1 above, q+r+t is 4–6, preferably 5; when W is H$_2$N—and Z is a six-membered Ar or Het ring, suitably q+t is 0–2, preferably 1; when W is H$_2$NC(=NH)—, and Z is (CH$_2$)$_t$, and U is chosen from group 1, suitably q+r+t is 3–5, preferably 4; when W is H$_2$NC(=NH)Z, is a six-membered Ar or Het ring, suitably q+r is 0 or 1, preferably 0.

Abbreviations and symbols commonly used in the peptide and chemical arts are used herein to describe the compounds of this invention. In general, the amino acid abbreviations follow the IUPAC-IUB Joint Commission on Biochemical Nomenclature as described in Eur. J. Biochem., 158, 9 (1984).

Arg refers to arginine, MeArg refers to Nα-methyl-arginine, HArg refers to homoarginine, NArg refers to norarginine, (Me$_2$)Arg refers to N',N"-dimethyl arginine, (Et2)Arg refers to N',N"-diethyl arginine and Orn refers to ornithine. These radicals are suitable components of the substituent R$^6$. Nα-Substituted derivatives of these amino acid are also useful in this invention. Representative methods for preparing α-substituted derivatives are disclosed in U.S. Pat. No. 4,687,758; Cheung et al., Can. J. Chem., 55,906 (1977); Freidinger et al., J. Org. Chem., 48, 77, (1982); and Shuman et al., PEPTIDES: PROCEEDINGS OF THE 7TH AMERICAN PEPTIDE SYMPOSIUM, Rich, D., Gross, E., Eds, Pierce Chemical Co., Rockford, Ill., 617 (1981), which are incorporated herein by reference.

C$_{1-4}$alkyl as applied herein is meant to include methyl, ethyl, n-propyl, isopropyl, n-butyl, isobutyl and t-butyl. C$_{1-6}$alkyl additionally includes pentyl, n-pentyl, isopentyl, neopentyl and hexyl and the simple aliphatic isomers thereof. C$_{0-4}$alkyl and C$_{0-6}$alkyl additionally indicates that no alkyl group need be present (e.g., that a covalent bond is present).

C$_{2-6}$ alkenyl as applied herein means an alkyl group of 2 to 6 carbons wherein a carbon-carbon single bond is replaced by a carbon-carbon double bond. C$_{2-6}$alkenyl includes ethylene, 1-propene, 2-propene, 1-butene, 2-butene, isobutene and the several isomeric pentenes and hexenes. Both cis and trans isomers are included.

C$_{2-6}$ alkynyl means an alkyl group of 2 to 6 carbons wherein one carbon-carbon single bond is replaced by a carbon-carbon triple bond. C$_{2-6}$ alkynyl includes acetylene, 1-propyne, 2-propyne, 1-butyne, 2-butyne, 3-butyne and the simple isomers of pentyne and hexyne.

C$_{1-4}$oxoalkyl refers to an alkyl group of up to four carbons wherein a CH$_2$ group is replaced by a C(O), or carbonyl, group. Substituted formyl, acetyl, 1-propanal, 2-propanone, 3-propanal, 2-butanone, 3-butanone, 1- and 4-butanal groups are representative. C$_{1-6}$oxoalkyl includes additionally the higher analogues and isomers of five and six carbons substituted by a carbonyl group. C$_{3-6}$oxoalkenyl and C$_{3-6}$oxoalkynyl refers to a C$_{3-6}$alkenyl or C$_{3-6}$alkynyl group wherein a CH$_2$ group is replaced by C(O) group. C$_{3-4}$oxoalkenyl includes 1-oxo-2-propenyl, 3-oxo-1-propenyl, 2-oxo-3-butenyl and the like.

A substituent on a C$_{1-6}$ alkyl, C$_{2-6}$ alkenyl, C$_{2-6}$ alkynyl or C$_{1-6}$ oxoalkyl group, such as R$^{11}$, may be on any carbon atom which results in a stable structure, and is available by conventional synthetic techniques.

Q-C$_{1-6}$ alkyl refers to a C$_{1-6}$ alkyl group wherein in any position a carbon-hydrogen bond is replaced by a carbon-Q bond. Q-C$_{2-6}$ alkenyl and Q-C$_{2-6}$ alkynyl have a similar meaning with respect to C$_{2-6}$ alkenyl and C$_{2-6}$ alkynyl.

Ar, or aryl, as applied herein, means phenyl or naphthyl, or phenyl or naphthyl substituted by one to three moieties R$^{11}$. In particular, R$^{11}$ may be C$_{1-4}$alkyl, C$_{1-4}$alkoxy, C$_{1-4}$alkthio, trifluoroalkyl, OH, F, Cl, Br or I.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazole, benzopyran, benzothiophene, furan, imidazole, indoline, morpholine, piperidine, piperazine, pyrrole, pyrrolidine, tetrahydropyridine, pyridine, thiazole, thiophene, quinoline, isoquinoline, and tetra- and perhydro- quinoline and isoquinoline. A six membered ring heterocycle containing one or two nitrogens, such as piperidine, piperazine, tetrahydropyridine and pyridine, are preferred heterocycles for the moiety Z. Any accessible combination of up to three substituents, such as chosen from R$^{11}$, on the Het ring that is available by chemical synthesis and is stable is within the scope of this invention. A six membered monocydic ring heterocycle containing one or two nitrogens, such as piperidine, piperazine, tetrahydropyridine and pyridine, are preferred heterocycles for the moiety Z.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as chosen from $R^{11}$, on the cycloalkyl ting that is available by conventional chemical synthesis and is stable, is within the scope of this invention.

An accessible substituted six-membered ting as referred to herein is any saturated or unsaturated six-membered ring which (i) has up to four substituents, such as R or R*, wherein the substituents may be present on any atom or heteroatom that results in a stable structure, and (ii) contains up to two heteroatoms selected from the group of N, O and S, wherein S and N may optionally be oxidized, and (iii) is stable and may be synthesized by one skilled in the chemical arts in a form fused via two adjacent ting carbon atoms to a phenyl, pyridyl, pyrazinyl, pyridazinyl or pyrimidinyl ting. Typical of accessible six-membered tings are the common saturated and unsaturated tings of cyclohexane, piperidine, piperazine, morpholine and thiomorpholine. Preferably, no two adjacent atoms in the seven-membered ting are simultaneously heteroatoms.

An accessible substituted aromatic six-membered ting as referred to herein is an unsaturated (e.g. aromatic) six-membered ting which (i) has one to three substituents, such as chosen from $R^6$ and $R^{11}$, (ii) optionally contains up to two nitrogens, (iii) is fused via two adjacent carbon atoms to an accessible substituted six-membered ting, and (iv) is stable and may be prepared by one skilled in the chemical arts. Typical of accessible aromatic six-membered tings are phenyl, pyridyl, pyrazinyl, pyridazinyl or pyrimidinyl ring. Representative bicyclic rings formed by the combination of the accessible aromatic six- and six-membered tings are: tetralin, quinoline, dihydroquinoline, tetrahydroquinoline, isoquinoline, dihydroisoquinoline, tetrahydroisoquinoline, quinazoline, dihydroquinazoline, tetrahydroquinazoline, 3,4-dihydro-2H-1,4-benzoxazine, and 3,4-dihydro-2-H-1,4-benzothiazine. Phenyl is a preferred accessible aromatic six-membered ting, and piperidine is a preferred accessible six-membered ring. Thus the preferred ring system is the 1,2,3,4-tetrahydroisoquinoline system.

It will be understood that, with respect to $A^1$–$A^4$, $CR^1R^{1'}$—$CR^4R^{4'}$ and $NR^1$–$NR^4$ are saturated sp$^3$ carbon and nitrogen atoms respectively which are singly bonded to the adjacent ring atoms, except that when $R^1/R^{1'}$, $R^2/R^{2'}$, $R^3/R^{3'}$, and $R^4/R^{4'}$ represent a doubly bonded substituent exo to the ring (e.g., such as =O or an alkylene side chain), $CR^1R^{1'}$—$CR^4R^{4'}$ may also represent an sp$^2$ carbon atom. It will be further understood that, with respect to $A^1$–$A^4$, $CR^1$–$CR^4$ and N represent an unsaturated sp$^2$ carbon or nitrogen atom, which may be connected by an endocydic double bond to an adjacent atom in the ring, provided such arrangement results in the creation of a stable compound.

Ⓝ as used herein indicates a nitrogen heterocycle, which may be a saturated or unsaturated stable five-, six- or seven-membered monocyclic ring, or a seven- to ten-membered bicyclic ring containing up to three nitrogen atoms or containing one nitrogen atom and a heteroatom chosen from oxygen and sulfur, and which may be substituted on any atom that results in a stable structure. The nitrogen atom in such ring may be substituted so as to result in a quaternary nitrogen. The nitrogen heterocycle may be substituted in any stable position by $R^{20}$, for instance H, $C_{1-4}$alkoxy, F, Cl, Br, I, $NO_2$, $NR'_2$, OH, $CO_2R'$, $CONHR'$, $CF_3$, Q-$C_{0-4}$alkyl, Q-$C_{1-4}$alkyl-S(O)$_u$ (e.g., where u is 0, 1 or 2) or $C_{1-4}$alkyl substituted by any of the aforementioned substituents.

Representative of Ⓝ are pyrroline, pyrrolidine, imidazole, imidazoline, imidazolidine, pyrazole, pyrazoline, pyrazolidine, piperidine, piperazine, morpholine, pyridine, pyridinium, tetrahydropyridine, tetrahydro- and hexahydroazepine, quinuclidine, quinuclidinium, quinoline, isoquinoline, and tetra- and perhydro- quinoline and isoquinoline. In particular, Ⓝ (may be pyridyl, pyrolidinyl, piperidinyl, piperazinyl, azetidinyl, quinuclidinyl or tetrahydropyridinyl. Ⓝ (is preferably 4-pyridyl, 4-(2-amino-pyridyl), 4-tetrahydropyridyl, 4-piperidinyl or 4-piperazinyl.

AA1 as referred to herein is an amino acid with its carboxyl group optionally protected, wherein the amino acid may be any of the natural α-amino acids or penicillamine. The unprotected carboxyl group is a free carboxylic add group. Protecting groups for the carboxyl are esters or amides which are formed, for instance, when the OH of the carboxy group is replaced by $R^8$. AA2 is an amino acid, as above, with its amino group optionally protected. Amino protecting groups are well known in the art, for instance, when the amino group is substituted by $R^{12}$. An unprotected amino group is a free $NH^2$ group.

C(O) indicates a carbon doubly bonded to oxygen (e.g., carbonyl), C(S) indicates a carbon doubly bonded to sulfur (e.g., thiocarbonyl).

t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. MeArg is Net-methyl arginine. Tet refers to 5-tetrazolyl.

DCC refers to dicyclohexylcarbodiimide, DMAP refers to dimethylaminopyridine, DIEA refers to diisopropylethyl amine, EDC refers to N-ethyl-N'(dimethylaminopropyl)-carbodiimide. HOBt refers to 1-hydroxybenzotriazole, THF refers to tetrahydrofuran, DIEA refers to diisopropylethylamine, DMF refers to dimethyl formamide, NBS refers to N-bromo-succinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of the formula (IV) with a compound of the formula (V):

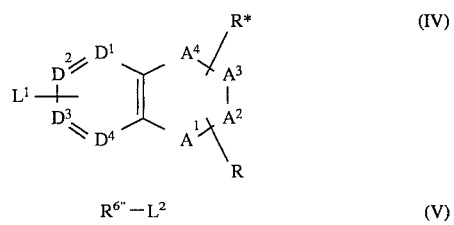

$$R^{6"}-L^2 \quad (V)$$

wherein $D^1$–$D^4$ and $A^1$–$A^4$, R and R* are as defined in formula (I), with any reactive functional groups protected;

$L^1$ and $L^2$ are functional groups which are capable of reacting to form the linkage —$(CR'R^{10})_r$—U—$(CR'_2)_{s-V-}$; and $R^{6''}$ is W—$(CR'_2)_q$—Z—and any portion of the group —$(CR'R^{10})_r$—U—$(CR'_2)_s$—V— which is connected to $L^2$, with any reactive functional groups protected;

and thereafter removing any protecting groups, and optionally forming a pharmaceutically acceptable salt.

It will be apparent that the precise identity of L and $L^2$ will be dependent upon the site of the linkage being formed. General methods for preparing the linkage —$(CR'R^{10})_r$—U—$(CR'_2)_s$—V— are described, for example, in EP-A 0 372 486 and EP-A 0 381 033 and EP-A 0 478 363, which are incorporated herein by reference.

For instance, if V is CONH, L may be —$NH_2$, $L^2$ may be OH (as in an acid) or Cl (as in an acid chloride), and $R^{6''}$ may be W—$(CR'_2)_q$—Z—$(CR'R^{10})_r$—U—$(CR'_2)_s$—C(O), with any functional groups optionally protected. For example, $R^{6''}$ may be (benzyloxycarbonyl-amidino)benzoyl- or ($N^\alpha$-Boc,$N^{guan}$-Tos)arginyl-. When $L^2$ is OH, a coupling agent is used.

Similarly, if V is NHCO, $L^1$ may be —$CO_2H$ or CO—Cl, $L^2$ may be —$NH_2$, and $R^{6''}$ may be W—$(CR'_2)_q$—Z—$(CR'R^{10})_r$—U—$(CR'_2)_s$—. For example, $R^{6''}$ may be (benzyloxycarbonyl-amidino)phenyl, (benzyloxycarbonylamino)methylbenzyl- or 6-(benzyloxycarbonylamino)hexyl-.

Where V is $NHSO_2$, $L^1$ may be $SO_2Cl$, $L^2$ may be —$NH_2$ and $R^{6''}$ may be as above. Where V is $SO_{02}NH$, $L^1$ may be —$NH_2$ and $L^2$ may be $SO_2Cl$. Methods to prepare such sulfonyl chlorides are disclosed, for instance, in J. Org. Chem., 23, 1257 (1958).

If V is CH=CH, $L^1$ may be —CHO, $L^2$ may be CH=P—$Ph_3$ and $R^{6''}$ may be W—$(CR'_2)_q$—Z—$(CR'R^{10})_r$—U—$(CR'_2)_s$—. Alternately, $L^1$ may be CH=P—$Ph_3$, $L^2$ may be CHO, e.g., $R^{6''}$ may be W—$(CR'_2)_q$—Z—$(CR'R^{10})_r$—U—$(CR'_2)_s$—1—CHO.

Where V is $CH_2CH_2$ may be obtained by reduction of a suitably protected compound wherein V is CH=CH.

Where V is $CH_2O$, $CH_2N$ or C≡C, $L^1$ may be —OH, —NH or —C≡CH, respectively; $L^2$ may be —Br; and $R^{6''}$ may be W—$(CR'_2)_q$—Z—$(CR'R^{10})_r$—U—$(CR'_2)_s$—. For example, $R^{6''}$ may be (benzyloxycarbonylamino)-methylbenzyl- or 2-(N-benzyl-4-piperidinyl)-ethyl. Similarly where U or V is $OCH_2$, $NR'CH_2$ or, $L^1$ may be -$CH_2Br$ and $L^2$ my be —OH, —NH or —H, respectively. Alternately, when U or V is C≡C, $L^1$ may be Br, I or $CF_3SO_3$, $L^2$ may be C≡CH and the coupling may be catalyzed by palladium and a base.

Compounds wherein V is $CHOHCH_2$ may be prepared from a suitably protected compound where V is CH=CH by the procedure disclosed in J. Org. Chem., 54, 1354 (1989).

Compounds wherein V is $CH_2CHOH$ may be obtained from a suitably protected compound where V is CH=CH by hydroboration and basic oxidation as disclosed in Tet. Lett., 31, 23 1 (1990).

The compounds of formula (IV), wherein one of $A^2$ or $A^3$ is nitrogen, are tetrahydroisoquinolines and are prepared by the general methods illustrated by Schemes 1–2. Representative methods for preparing tetrahydroisoquinolines are well known in the art (e.g., Kametani and FuKumoto, Isoquinolines, ed. G. Grethe, Wiley-Interscience, New York, 1981, p. 139 and Gilchrist, Heterocyclic Chemistry, Pitman Publishing, London, 1985, p.272. In the Schemes, $R^{1''}$–$R^{7''}$ indicate $R^1$–$R^7$ or a suitable precursor thereof, wherein any functional groups are protected as known in the art.

Scheme I

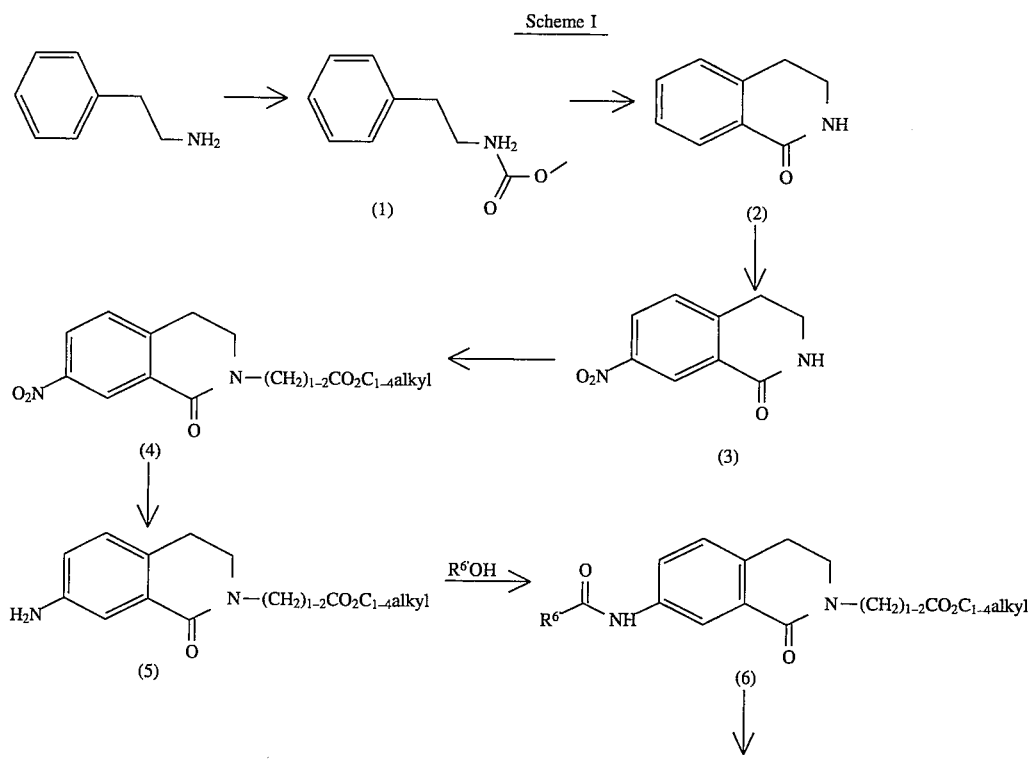

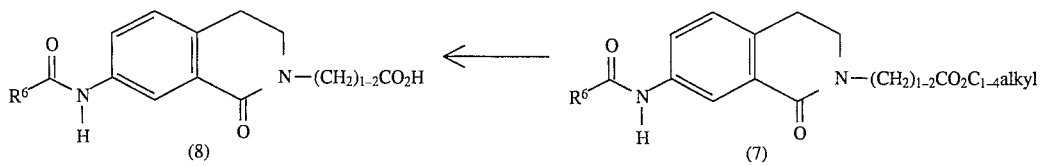

Scheme I provides a method for preparing compounds wherein $A^1$ is C=O, $A^2$ is $NR^2$, $A^3$ is $CH_2$ and $A^4$ is $CH_2$. Generally, the synthesis begun with a phenethylamine. Acylation of this starting material with, for example, chloromethylformate in the presence of a base, such as triethylamine, in a suitable solvent, such as tetrahydrofuran, yields formula (1) compounds. Cyclization of (1) under acidic conditions, for example, using polyphosphoric acid at, elevated temperatures, preferably at, about 140° C., results in the formation of the 1,2,3,4-tetrahydroisoquinolin-1-one ring system represented by formula (2). The compound of formula (2) is nitrated using, for example, potassium nitrate in sulfuric acid. the nitrogen of the tetrahydroisoquinolin-1-one is then alkylated. For compounds in which the —$CH_2CO_2C_{1-4}$alkyl, the formula (3) compound is reacted with a $C_{1-4}$alkyl haloacetate, such as methyl bromoacetate, in the presence of a base, such as sodium, lithium or potassium hydride, preferably sodium hydride, in a suitable solvent, such as tetrahydrofuran. For compounds in which the $R^2$ group is —$CH_2CH_2CO_2C_{1-4}$alkyl, the formula (3) compound is reacted with a $C_{1-4}$alkyl acrylate, such as methyl acrylate, in the presence of a base, such as sodium methoxide, in a suitable solvent, such as methanol. Selective reduction of the nitro group, such as with hydrogenation over a palladium on carbon catalyst, provides the formula (5) amine compounds, which are acylated/coupled with a suitably protected carboxylic acid, $R^{6''}$—OH, for example 4-Cbz-amidinobenzoic acid. The condensation of the amino group with the $R^{6''}$—OH, wherein $R^{6''}$ is as defined in formula (V), is carried out in the presence of an amide-forming agent, such as water-soluble carbodiimide, in the presence of 1-hydroxybenzotriazole and a base, such as diisopropylethylamine, in a suitable solvent, such as dimethylformamide. Protecting groups, such as those for amino or carboxy groups, are selectively removed by methods known in the art. For example, a Cbz-group on a nitrogen atom may be removed by hydrogenation in the presence of a catalyst, such as palladium on carbon, in an acidic medium, such as in ethereal hydrochloric acid/methanol and a $C_{1-4}$alkyl ester group on a carboxylic acid moiety may be removed by saponification using base, for example sodium hydroxide, in a suitable solvent system, such as water/methanol.

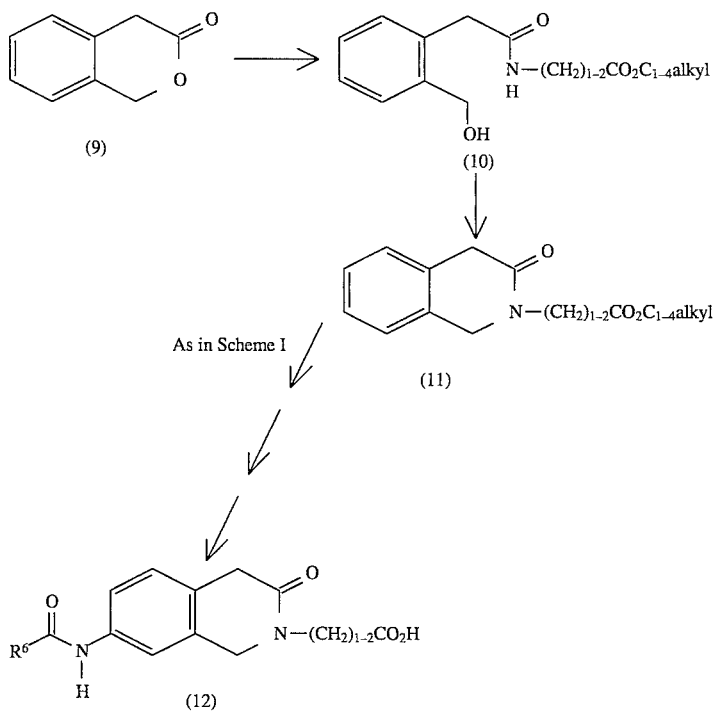

Scheme II provides a method for preparing compounds wherein $A^1$ is $CH_2$, $A^2$ is $NR^2$, $A^3$ is C=O and $A^4$ is $CH_2$. According to Scheme II, isochroman-3-one, which is a formula (9) compound, is reacted with a glycine $C_{1-4}$ alkyl ester, such as glycine methyl ester, in the presence of a base, such as triethylamine, in a suitable solvent, such as methanol, to give a compound of formula (10). Cyclization of (10) using, for example, triphenylphosphine and diethyl azodicarboxylate in a suitable solvent, such as tetrahydrofuran, results in the formation of the 1,2,3,4-tetrahydroisoquinolin-3-one ring system represented by formula (11 ). The nitration, reduction, acylation, and deprotection steps are then carrier out as detained in Scheme I, to give formula (12) compounds, which are also formula (I) compounds.

Coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to form peptide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.*, 29, 984 (1986) and *J. Med. Chem.*, 30, 2291 (1987) are generally illustrative of the technique and are incorporated herein by reference.

Solution synthesis for the formation of amide or peptide bonds is accomplished using conventional methods used to form amide bonds. Typically, the amine or aniline is coupled via its free amino group to an appropriate carboxylic acis substrate using a suitable carbodiimide coupling agent, such as N,N 'dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or add halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran-(THF), in the presence of a base, such as N-methyl morpholine, DMAP or a trialkylamine, with isobutyl chloroformate to form the "activated anhydride, which is subsequently reacted with the free amine of a second protected amino acid or aniline.

Compounds of formula (V) are prepared by conventional methods known in the art from commercially available materials. W is a generally a basic functional group attached to Z, optionally via an alkyl chain, and is protected during the synthesis of $R^6$ or is introduced into the molecule after the-$(CR'R^{10})_r$—U—$(CR'_2)_s$—V— linkage has been formed. For example, compounds of formula (XII) or formula (I) wherein W is a suitably substituted R'R"N—, R"R'NC(=NR'), $R'_2N(R^{13})C=N-$, R"N=$(R^{13})C$—NR'—, $R'_2N(R'_2N)C=N-$ or R"R'N(R'N=)C—NR', are prepared by conventional methods including those disclosed in EP-A 0 372 486, EP-A 0 381 033 or EP-A 0 478 363, which are incorporated herein by reference.

Compounds of formula (V) wherein W is ⓝ are prepared, inter alia, by methods disclosed in EP-A 0 478 363.

Compounds wherein W is $R'_2N(R'_2N)C=N-X-$ or R"R 'N(R'N=)C—NR'—X—, and X is O are prepared, inter alia, by methods disclosed in *J. Org. Chem.*, 51, 5047 (1986).

Compounds wherein W is $R'_2N(R'_2N)C=N-X-$ or R"R'N(R'N=)C—NR'—X—, and X is N=CR', are prepared, inter alia, by methods disclosed in U.S. Pat. No. 3,714,253 and Eur. *J. Med. Chem. Chim. Ther.*, 20, 25 (1985).

Compounds wherein W is $R'_2N(R'_2N)C=N-X-$ or R"R'N(R'N=)C—NR'—X—, and X is C(O), are prepared, inter alia, by methods disclosed in U.S. Pat. No. 3,714,253 and *Can. J. Chem.*, 43, 3103 (1965).

Compounds wherein W is R'ONR'C(=NR')—may be prepared, inter alia, by methods disclosed in *J. Het. Chem.*, 16, 1063 (1979) or *J. Het. Chem.*, 26, 125 (1989).

Compounds wherein W is $R'_2NR'NC(=NR')$—are prepared by conventional methods including those disclosed in Syn., 583 (1974).

Compounds wherein W is R'R"NR'N—are prepared, inter alia, by methods disclosed in *J. Prakt. Chem.*, 36, 29 (1967).

Compounds wherein W is R'R"NR'NCO—are prepared, inter alia, by methods disclosed in *Bull. Chem. Soc. Jpn.*, 43, 2257 (1970).

Compounds wherein W is R"R'NC(=NR')Y, and Y is S, are prepared, inter alia, by methods disclosed in *Chem. Lett.*, 1379 (1986).

Compounds of formula (V) or formula (I), wherein W is R"R'NC(=NR')Y and Y is O, are prepared by conventional methods including those disclosed in Japanese Patent 2022751.

Useful intermediates of formula (V) include compounds of the formula W'—$(CR'_2)_q$—Z—$(CR'R^{10})_r$—U—$(CR'_2)_s$—$L^2$, wherein Z, R', R", $R^{10}$, U, q, r, and s are as defined for formula (I); $L^2$ is CHO, $CO_2R'$, OH, Cl, Br, I, $CH_2$-T or NR'R", and T is $CF_3SO_3$, OH, NHR", Cl, Br or I; and W' is W with any reactive basic nitrogen group protected as herein described. $R'SO_2$, R'OCO and R'CO (e.g., Tos, Boc, Cbz or acetyl) are typical nitrogen protecting groups. Particular examples of such intermediates are:

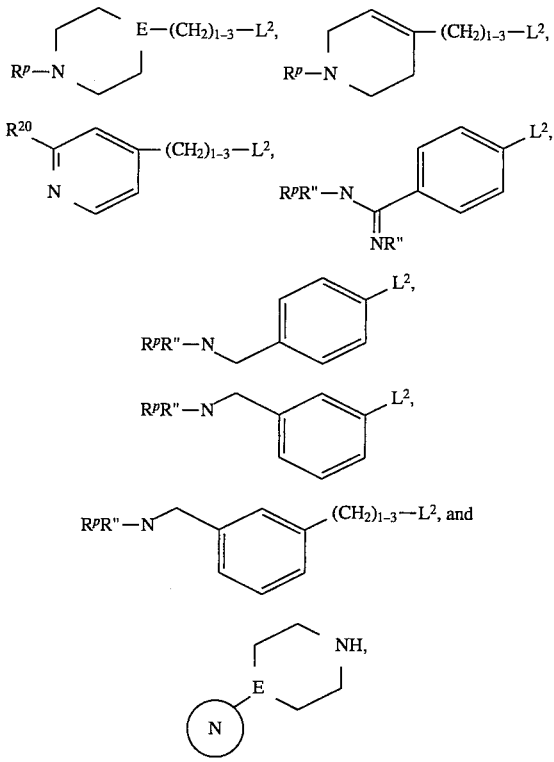

wherein E is N or CH, $R^{20}$ is hydrogen, amino, mono or di-$C_{1-4}$alkylamino, hydroxy or $C_{1-4}$alkyl.

The reactive functional groups of the sidechains of each synthetic fragment are suitably protected as known in the art. Suitable protective groups are disclosed in Greene, PROTECTIVE GROUPS IN ORGANIC CHEMISTRY, John Wiley and Sons, New York, 1981. For example, the Boc, Cbz, phthaloyl or Fmoc group may be used for protection of an amino or amidino group. The Boc group is generally preferred for protection of an α-amino group. A t-Bu, cHex or benzyl ester may be used for the protection of the side chain carboxyl. A benzyl group or suitably substituted benzyl group (e.g., 4-methoxy-benzyl or 2,4-dimethoxybenzyl) is used to protect the mercapto group or the hydroxyl group. The tosyl group may be used for protection of the imidazolyl group and tosyl or nitro group for protection of the guanidino group. A suitably substituted carbobenzyloxy group or benzyl group may be also be used for the hydroxyl group or amino group. Suitable substitution of the carbobenzyloxy or benzyl protecting groups is ortho and/or para substitution with chloro, bromo, nitro or methyl, and is used to modify the reactivity of the protective group. Except for the Boc group, the protective groups for the amino moiety are, most conveniently, those which are not removed by mild add treatment. These protective groups are removed by such methods as catalytic hydrogenation, sodium in liquid ammonia or HF treatment, as known in the art.

Modification of amino groups especially on the six-membered ring of the bicyclic system, may be accomplished by alkylation, sulfonylation, cyanation or acylation as is generally known in the art.

Acid addition salts of the compounds of this invention are prepared in a standard manner in a suitable solvent from the parent compound and an excess of an add, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li+, Na+, K+, Ca++, Mg++ and NH$_4$+ are specific examples of cations present in pharmaceutically acceptable salts.

This invention provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, the compounds of this invention may be encapsulated, tabletted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or nonaqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds of this invention may be used in vitro to inhibit the aggregation of platelets in blood and blood products, e.g., for storage, or for ex vivo manipulations such as in diagnostic or research use.

This invention also provides a method of inhibiting platelet aggregation and clot formation in a mammal, especially a human, which comprises the internal administration of a compound of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TIP), snake venom and immune diseases, are likely to be responsive to such treatment. In addition, the compounds of this invention may be useful in a method for the prevention of metastatic conditions, the prevention or treatment of fungal or bacterial infection, inducing immunostimulation, treatment of sickle cell disease, and the prevention or treatment of diseases in which bone resorption is a factor.

The compounds of formula (I) are administered either orally or parenterally to the patient, in a manner such that the concentration of drug in the plasma is sufficient to inhibit platelet aggregation, or other such indication. The pharmaceutical composition containing the compound is administered at a dose between about 0.2 to abotit 50 mg/kg in a manner consistent with the condition of the patient. For acute therapy, parenteral administration is preferred. For persistent states of hyperaggregability, an intravenous infusion of the peptide in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The compound of this invention is administered one to four times daily at a level of about 0.4 to about 50 mg/kg to achieve a total daily dose of about 0.4 to about 200 mg/kg/day.

This invention further provides a method for inhibiting the reocclusion of an artery or vein following fibrinolytic therapy, which comprises internal administration of a compound of formula (I) and a fibrinolytic agent. It has been found that administration of an peptide in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants, thereof, which retain plasminogen activator activity, such as variants which have been chemically modified or in which one or more amino acids have been added, deleted or substituted or in which one or more functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural' sources, but are commonly produced by traditional methods of genetic engineering.

Useful formulations of tPA, SK, UK and pUK are disclosed, for example, in EP-A 0 211 592, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compound of formula (I) and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The compound of formula (I) is administered just prior to, at the same time as, or just after parenteral administration of tPA or other fibrinolytic agent. It may prove desirable to continue treatment with the peptide for a period of time well afar reperfusion has been established to maximally inhibit post-therapy reocclusion. The effective dose of tPA, SK, UK or pUK may be from 0.5 to 5 mg/kg and the effective dose of the compound of this invention may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of the peptide inhibitor followed by an infusion of the fibrinolytic agent.

The pharmacological activity of the compounds of this invention is assessed by their ability to inhibit the binding of $^3$H-SK&F 107260, a known RGD-fibrinogen antagonist, to the GPIIbIIIa receptor; their ability to inhibit platelet aggregation, in vitro, and their ability to inhibit thrombus formation in vivo.

Inhibition of RGD-mediated GPIIb-IIIa binding

Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM CaCl$_2$ at 4° C. for 2 h. The lysate was centrifuged at 100,000 g for 1 h. The supernatant obtained was applied to a 5 ml, lentil lectin sepharose 4B column (E. Y. Labs) preequilibrated with 20 mM Tris-HCl, pH 7.4, 100 mM NaCl, 2 mM CaCl$_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIFn-IIIa obtained was >95% pure as shown by SDS polyacrylamide gel electrophoresis.

Incorporation of GPIIb-IIIa in Liposomes.

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl$_2$ (with 2 changes). The GPIIb-IIIa-containing liposomes wee centrifuged at 12,000g for 15 rain and resuspended in the dialysis buffer at a final protein concentration of approximately 1 mg/mL. The liposomes were stored at −70° C. until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 am hydrophilic durapore membranes. The wells were precoated with 0.2 mL of 10 µg/mL polylysine (Sigma Chemical Co., St. Louis, Mo.) at room temperature for 1 h to block nonspecific binding. Various concentrations of unlabeled benzadiazapines were added to the wells in quadruplicate. [$^3$H]-SK&F-107260 was applied to each well at a final concentration of 4.5 nM, followed by the addition of 1 µg of the purified platelet GPIIb-IIIa-containing liposomes. The mixtures were incubated for 1 h at room temperature. The GPIIb-IIIa-bound [$^3$H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif. in a Beckman Liquid Scintillation Counter (Model LS6800), with 40% efficiency. Nonspecific binding was determined in the presence of 2 M unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: $Ki = IC50/(1+L\ Kd)$, where L is the concentration of [$^3$H]-SK&F-107260 used in the competitive binding assay (4.5 nM), and Kd is the dissociation constant of [$^3$H]-SK&F-107260 which is 4.5 nM as determined by Scatchard analysis.

Inhibition of Platelet Aggregation

Blood was collected (citrated to prevent coagulation) from, naive, adult mongrel dogs. Platelet rich plasma, PRP, was prepared by centrifugation at 150×g for 10 min at room temperature. Washed platelets were prepared by centrifuging PRP at 800×g for 10 min. The cell pellet thus obtained was washed twice in Tyrode's buffer (pH 6.5) without $Ca^{++}$ and resuspended in Tyrode's buffer (pH 7.4) containing 1.8 mM $Ca^{++}$ at $3\times10^5$ cells/mi. Peptides were added 3 rain prior to the agonist in all assays of platelet aggregation. Final agohist concentrations were 0.1 unit/ml thrombin and 2 mM ADP (Sigma). Aggregation was monitored in a Chrono-Log Lumi-Aggregometer. Light transmittance 5 rain after addition of the agonist was used to calculate percent aggregation according to the formula % aggregation $=[(90-CR) \div (90-10)]\times 100$, where CR is the chart reading, 90 is the baseline, and 10 is the PRP blank reading. IC50's were determined by plotting [% inhibition of aggregation]vs. [concentration of peptide]. Peptides were assayed at 200 mM and diluted sequentially by a factor of 2 to establish a suitable dose response curve.

To assess the stability of the compounds to plasma proteases, the compounds were incubated for 3 h (rather than 3 min) in the PRP prior to addition of the agonist.

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629 (1980).

The examples which follow are intended to in no way limit the scope of this invention, but are provided to illustrate how to make and use the compounds of this invention. Many other embodiments will be readily apparent and available to those skilled in the art.

EXAMPLE 1

Preparation of 7-[4-Amidinobenzamide]-2-carboxymethyl-1,2,3,4-tetrahydroisoauinolin-1-one a) N-methoxycarbonyl-phenethylamine To a cold solution consisting of phenethylamine (20g, 0.16mol) in tetrahydrofuran (900 mL) was added triethylamine (23 mL, 0.16 mol). To this solution was added dropwise chloromethylformate (64 mL, 0.8 mol). The reaction mixture was then stirred overnight water (450 mL) was added and the layers were separated. The organic layer was washed successively with water (1×200mL) and brine (1×200mL). The organic solvent was dried (anhydrous magnesium sulfate), filtered and concentrated to give the title compound (28 g, 94% yield).

b) 1,2,3,4-tetrahydroisoquinolin-1-one

To a solution of polyphosphric acid (200 mL) at 140° C. N-methoxycarbonyl-phenethylamine (28 g, 0.16 mol) was added portionwise over a 5 hour period. The reaction solution was poured into cold water (400 mL) and extracted with methylene chloride (5×200 mL). The organic layers were combined, dried with anhydrous magnesium sulfate, filtered and concentrated to give the title compound (17.96 g, 86% yield).

c) 7-nitro-1,2,3,4-tetrahydroisoquinolin-1-one

To a cold solution consisting of potassium nitrate (8.2 g, 81.6 mmol) in sulfuric acid (40 mL) was added 1,2,3,4-tetrahydroisoquinolin-1-one (10 g, 68mmol) dropwise over a period of five minutes. The reaction mixture was stirred overnight at room temperature and then poured into ice. The solution was filtered. After washing with water several times, the solid was dried to yield the title compound (9.85 g, 76%).

d) 2-methylcarbonylmethoxy-7-nitro-1,2,3,4-tetrahydroisoquinolin-1-one

To a solution of 7-nitro-1,2,3,4-tetrahydroisoquinolin-1-one (2.0 g, 10.4 mmol) in tetrahydrofuran (300 mL) was added sodium hydride (500 mg, 60% suspension in oil, 12.5 mmol). To the resulting mixture was added methyl bromoacetate (1.1 mL, 11 mmol). After 3 hours, ethyl acetate (20 mL) was added followed by water (25 mL). The solution was concentrated and the resulting oil was partitioned between ethyl acetate and water (1:1,200 mL). The layers were separated and the organic layer was washed successively with water (1×100 mL) and brine (1 ×100 mL). The organic layer was dried with anhydrous magnesium sulfate, filtered and concentrated. The residue was treated with ethyl acetate and a solid formed. The solution was filtered to give the title compound (1.6 g, 55% yield).

e) 7-amino-2-methylcarbonylmethoxy-1,2,3,4-tetrahydroisoquinolin-1-one

A solution consisting of 2-methylcarbonylmethoxy-7-nitro-1,2,3,4-tetrahydroisoquinolin-1-one (500 mg, 1.9 mmol), 10% palladium on carbon (80 mg) and methanol (70 mL) was hydrogenated at 40 psi for 1 hour. The solution was filtered through Celite® and concentrated to give the title compound (400 mg, 90% yield).

f) 7-[4-Cbz-amidinobenzamide]-2-methylcarbonylmethoxy-1,2,3,4-tetrahydroisoquinolin-1-one To a solution consisting of 7-amino-2-methylcarbonylmethoxy-1,2,3,4-tetrahydroisoquinolin-1-one (400 mg, 1.7 mmol) in dimethylformamide (5 mL) was added diisopropylethylamine until the pH was 7.5. To this solution was added consecutively 1-hydroxybenzotriazole (310 mg, 2.0 mmol), 4-Cbz-amidinobenzoic acid (611 mg, 2.0 mmol) and water-soluble carbodiimide (392 mg, 1.8 mmol). After two minutes dimethylaminopyridine (210 mg, 1.7 mmol) was added and the resulting solution was stirred at room temperature for 18 hours. The solution was concentrated and chromatographed using silica gel and ethyl acetate/hexane (7:3). Desired fractions were concentrated to give the title compound (426 mg, 48% yield).

g) 7-[4-amidinobenzamide]-2-methylcarbonylmethoxy-1,2,3,4-tetrahydroisoquinolin-1-one A solution consisting of 7-[1-Cbz-amidinobenzamide]-2-methylcarbonylmethoxy-1,2,3,4-tetrahydroisoquinolin-1-one (400 mg, 0.78 retool), 10% palladium on carbon (40 mg), 1M hydrochloric acid in diethyl ether (3 mL) and methanol (30 mL) was hydrogenated at 10 psi for 30 minutes. The solution was filtered through Celite® and concentrated to give the title compound (311 mg, quantitative).

h) 7-[4-amidinobenzamide]-2-carboxymethyl-1,2,3,4-tetrahydroisoquinolin-1-one

To a cold solution consisting of 7-[4-amidinobenzamide]-2-methylcarbonylmethoxy-1,2,3,4-tetrahydroisoquinolin-1-one (7) (320 mg, 0.8 mmol), methanol (3 mL) and water (2 mL) was added 1N sodium hydroxide (2.2 mL, 2.2 mmol). The solution was stirred at room temperature for 18 hours. The solution was concentrated and the residue was taken up in water (10 mL) and 1M hydrochloric acid was added dropwise until precipitation occurred. The solution was filtered and the solid was washed with water and dried in vacuo to give the title compound (90 mg, 31% yield). MS (FAB) m/e 367 [M+H]$^+$. HPLC (k'2.6 isocratic A:acetonitrile B: water-0.1% trifluoroacetic acid, 15% acetonitrile, UV detection at 220 nm) TLC Rf 0.5 (Pyridine:Acetic Acid:Butanol:water 15:5:10:10) 1H NMR (DMSO[d6]) shows absence of methyl ester protons.

EXAMPLE 2

Preparation of 7-[4-Amidinobenzamido]-2-carboxyethyl,- tetrahydroisoquinolin-1,-one a) 2-ethylcarbonylmethoxy-7-nitro-1,2,3,4-tetrahydroisoquinolin-1-one To a solution consisting of 7-nitro-1,2,3,4-tetrahydroisoquinolin-1-one (3.0 g, 15.6 mmol), methyl acrylate (15 mL, 156 mmol) and methanol (50 m L) was added sodium methoxide (840 mg, 15.6 mmol). The resulting solution was refluxed overnight. The reaction solution was concentrated and the resulting residue was introduced unto a silica gel column equilibrated with ethyl acetate/Hexane (3:7). Elution was done with the same solvent system. Desired fractions were concentrated to give title compound (2.6 g, 69% yield).

b ) 7-amino-2-ethylcarbonylmethoxy-1,2,3,4-tetrahydroisoquinolin-1-one

2-Ethylcarbonylmethoxy-7-nitro-1,2,3,4-tetrahydroisoquinolin-1-one was hydrogenated according to the procedure of Example 1 (e) to give the title compound.

c) 7-[4-Cbz-amidinobenzamide]-2-ethylcarbonylmethoxy-1,2,3,4-tetrahydroisoquinolin-1-one 7-Amino-2-ethylcarbonylmethoxy-1,2,3,4-tetrahydroisoquinolin-1one was coupled to 4-Cbz-amidinobenzoic acid according to the procedure of Example 1 (f) to give the title compound.

d) 7-[4-amidinobenzamide]-2-ethylcarbonylmethoxy-1,2,3,4-tetrahydroisoquinolin-1-one 7-[4-Cbz-amidinobenzamide]-2-ethylcarbonylmethoxy-1,2,3,4-tetrahydroisoquinolin-1-one was hydrogenated according to the procedure of Example 1 (g) to give the title compound.

e) 7-[4-amidinobenzamido]-2-carboxyethyl-1,2,3,4-tetrahydroisoquinolin-1-one

7-[4-Amidinobenzamide]-2-ethylcarbonylmethoxy-1,2,3,4-tetrahydroisoquinolin-1-one was hydrolyzed according to the procedure of Example 1 (h) to give the title compound.

EXAMPLE 3

Preparation of 7-[4-Amidinobenzamido],2-carboxymethyl-1,2,3,4-tetrahydroisoquinolin-3-one a) N-(2-hydroxymethyl-phenylacetamide)glycine methyl ester To a solution consisting of glycine methyl ester (9.2 g, 69 mmol) in methanol (60 mL) was added triethylamine (12.2 mL, 70 mmol), followed by the addition of isochroman-3-one (10 g, 67.6 mmol). The solution was stirred at room temperature for 18 hours. The solution was concentrated and the residue was purified on silica gel eluting with ethyl acetate/hexane (1:1). Desired fractions Were concentrated to give the title compound (10.7 g, 67% yield).

b) 2-methylcarbonylmethoxy-1,2,3,4-tetrahydroisoquinolin-3-one

N-(2-hydroxymethyl-phenylacetamide)glycine methyl ester (200 mg, 0.84 mmol), triphenylphosphine (221 mg, 0.84 mmol) and tetrahydrofuran (15 mL,) were mixed and to the resulting solution was added dropwise diethyl azodicarboxylate (133 microliters, 0.84 mmol)in tetrahydrofuran (10 mL,). The resulting solution was stirred at room temperature for 18 hours. The solution was concentrated and the residue was introduced onto a silica gel column equilibrated with ethyl acetate hexane (1:1). Elution was done with the same solvent system. Desired fractions were concentrated to give the title compound.

c) 2-methylcarbonylmethoxy-7-nitro-1,2,3,4-tetrahydroisoquinolin-3-one

Nitration on 2-methylcarbonylmethoxy-1,2,3,4-tetrahydroisoquinolin-3-one was carried out according to the procedure of Example 1 (d) to give the title compound.

d) 7-amino-2-methylcarbonylmethoxy-1,2,3,4-tetrahydroisoquinolin-3-one

2-Methylcarbonylmethoxy-7-nitro-1,2,3,4-tetrahydroisoquinolin-3-one was reduced according to the procedure of Example 1 (e) to give the title compound.

e) 7-[4-Cbz-amidinobenzamide]-2-methylcarbonylmethoxy-1,2,3,4-tetrahydroisoquinolin-3-one 7-Amino-2-methylcarbonylmethoxy-1,2,3,4-tetrahydroisoquinolin-3-one was coupled to 4-Cbz-amidinobenzoic acid according to the procedure of Example 1 (f) to give the title compound.

f) 7-[4-amidinobenzamide]-2-methylcarbonylmethoxy-1,2,3,4-tetrahydroisoquinolin-3-one 7-[4-Cbz-amidinobenzamide]-2-methylcarbonylmethoxy-1,2,3,4,-tetrahydroisoquinolin-3-one was deprotected according to the procedure of Example 1 (g) to give the title compound.

g) 7-[4-amidinobenzamide]-2-carboxymethyl-1,2,3,4-tetrahydroisoquinolin-3-one 7-[4- amidinobenzamide ]-2-methylcarbonylmethoxy-1,2,3,4-tetrahydroisoquinolin-3-one was hydrolyzed according to the procedure of Example 1 (h) to give the title compound.

EXAMPLE 4

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

EXAMPLE 5

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

EXAMPLE 6

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The foregoing is illustrative of the making and using of this invention. This invention, however, is not limited to the precise embodiments described herein, but encompasses all modifications within the scope of the claims which follow.

What is claimed is:

1. A compound of the formula:

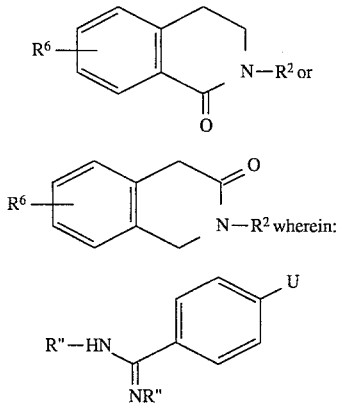

wherein:

$R^6$ is

U is NR'CO, CONR', $(CH_2)CO$, CH=CH, $CH_2O$, $OCH_2$ or $(CH_2)_2$;

$R^2$ is $R^7$, $CH_2R^7$ or $CH_2CH_2R^7$;

$R^7$ is $COR^8$, $COR'_2R^9$, $C(S)R^8$, $S(O)_mOR'$, $S(O)_mNR'R''$, or $NO_2$;

$R^8$ is —OR', —NR'R", —NR'SO$_2$R', —NR'OR', —OCR'$_2$C(O)OR', —OCR'$_2$OC(O)—R', —OCR'$_2$C(O)NR'$_2$ or CF$_3$;

$R^9$ is —OR', —CN, —S(O)$_r$R', S(O)$_m$NR'$_2$, —C(O)R'C(O)NR'$_2$ or —CO$_2$R';

R' is H, $C_{1-6}$alkyl, $C_{3-7}$cycloalkyl-$C_{0-4}$alkyl or Ar—$C_{0-4}$alkyl;

R" is R', —C(O)R' or —C(O)OR$^{15}$;

$R^{15}$ is H, $C_{1-6}$alkyl or Ar—$C_{0-4}$alkyl;

m is 1 or 2; and r is 0 to 2;

or pharmaceutically acceptable salts thereof.

2. A compound according to claim 1 which is:
7-[4-(amidinobenzamide)]-2-carboxymethyl-1,2,3,4-tetrahydroisoquinolin-1-one;

7-[4-(amidinobenzamido)]-2-carboxymethyl-1,2,3,4-tetrahydroisoquinolin-1-one; or 7-[4-(amidinobenzamide)]-2-carboxymethyl-1,2,3,4-tetrahydroisoquinolin-3-one;

or a pharmaceutically acceptable salt thereof.

3. A compound according to claim 1 which is 7-[4-(amidinobenzamide)]-2-carboxymethyl-1,2,3,4-tetrahydroisoquinolin-1-one or a pharmaceutically acceptable salt thereof.

4. A pharmaceutical composition comprising a compound according to claim 1 and a pharmaceutically acceptable carrier.

5. A method for effecting inhibition of platelet aggregation to a subject in need thereof which comprises administering a compound according to claim 1.

6. A method for treating stroke which comprises administering to a subject in need thereof a compound according to claim 1.

7. A method for treating transient ischemia attacks which comprises administering to a subject in need thereof a compound according to claim 1.

8. A method for treating myocardial infarction which comprises administering to a subject in need thereof a compound according to claim 1.

9. A method for promoting reperfusion of an artery or vein and inhibiting reocclusion which comprises administering to a subject in need thereof a fibrinolytic agent and a compound according to claim 1.

* * * * *